| United States Patent [19] | [11] | 4,442,844 |
|---|---|---|
| Navach | [45] | Apr. 17, 1984 |

[54] METHOD AND APPARATUS FOR MAKING PHYSIOLOGICAL MEASUREMENTS

[76] Inventor: Joseph H. Navach, 17240 Halsted St., Northridge, Calif. 91325

[21] Appl. No.: 297,513

[22] Filed: Aug. 28, 1981

[51] Int. Cl.³ ............................................. A61B 10/00
[52] U.S. Cl. .................................... 128/663; 128/664
[58] Field of Search ............... 128/633, 663, 664–665, 128/687–690

[56] References Cited

U.S. PATENT DOCUMENTS

| 3,661,146 | 5/1972 | Peronneau et al. | 128/663 |
|---|---|---|---|
| 3,987,673 | 10/1976 | Hansen | 128/663 X |
| 4,086,915 | 5/1978 | Kofsky et al. | 128/633 |
| 4,191,195 | 3/1980 | Miller | 128/908 X |
| 4,227,407 | 10/1980 | Drost | 128/663 X |
| 4,321,930 | 3/1982 | Jöbsis et al. | 128/633 |
| 4,336,808 | 6/1982 | Ohno et al. | 128/663 |

*Primary Examiner*—Kyle L. Howell
*Assistant Examiner*—Francis J. Jaworski

*Attorney, Agent, or Firm*—Edward D. O'Brian; K. H. Boswell

[57] ABSTRACT

Measurements having physiological significance can be obtained by analyzing radiation which is reflected by an artery of the body. Such measurements are preferably made by immobilizing a part of the body such as the human wrist where an artery extends substantially linearly and is adjacent to and generally parallel with the surface of the skin, by then directing radiation from a radiation source or sending apparatus toward any of several specific locations along the artery at an angle such that some of the radiation will be reflected, and by next measuring the amount of reflected radiation in accordance with time through the use of a receiving or detection apparatus. These locations are specific regions or areas generally along and generally extending transverse to the artery which have been established on the basis of experience as normally being capable of reflecting back at least some radiation in an amount having physiological significance.

25 Claims, 7 Drawing Figures

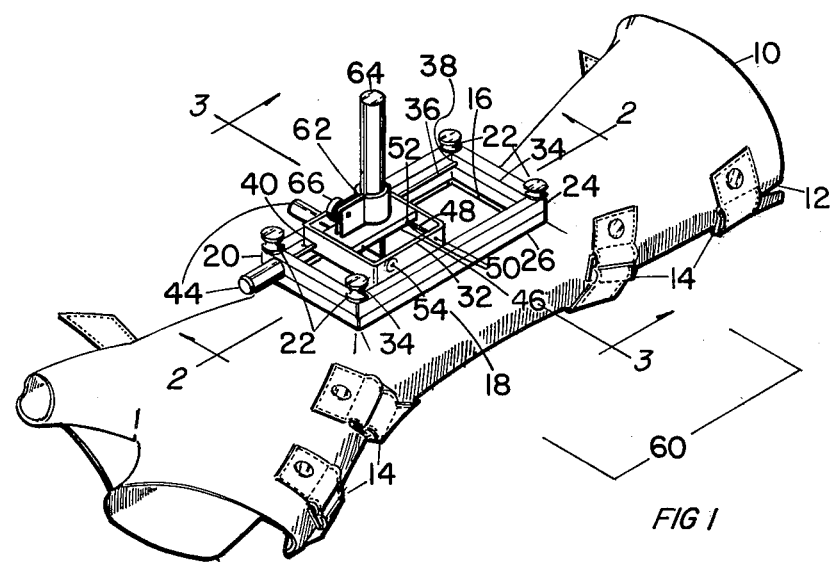
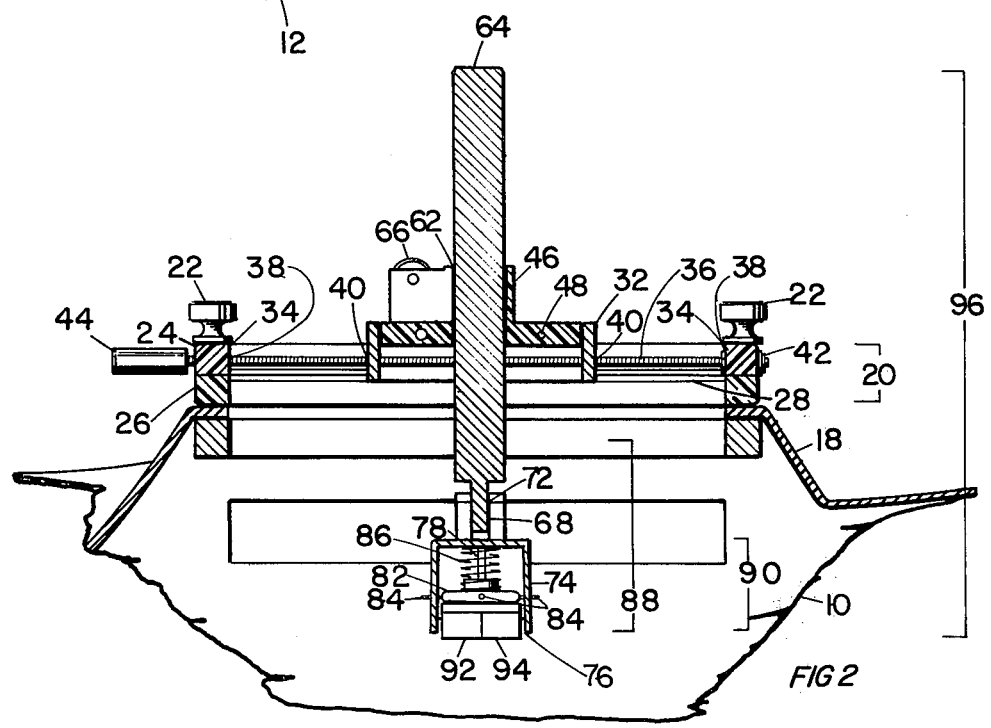

METHOD AND APPARATUS FOR MAKING PHYSIOLOGICAL MEASUREMENTS

BACKGROUND OF THE INVENTION

This invention pertains to a new and improved method and apparatus for making physiological measurements.

Although the present invention is considered to primarily relate to making physiological measurements, it is inherently related to the field of medicine because of the nature of such measurements. More specifically, the invention is inherently related to that branch of medicine which is referred to as "auricular medicine". This term "auricular medicine" was originally adopted as a result of certain discoveries by a Dr. Paul Nogier relative to stimulation of the auricle or ear resulting in a change or variation in the pulse at a particular location along the radial artery in the human wrist. Because it was recognized that this change or variation was related to the autonomic nervous system the pulse at such a particular location has been referred to as the vascular autonomic signal or VAS pulse.

Although it was recognized by Dr. Nogier and others that the VAS pulse had the potential of being utilized for a variety of medical purposes the VAS pulse has been used very little for such purposes. It is considered there are a number of reasons for this. One of these is that it has been difficult utilizing past methods to satisfactorily measure the VAS pulse. Unfortunately, the "ability" to "read" the pulse passed by many acupuncturists does not amount to "measurement" in a current instrumentation sense and is probably impossible for various individuals to acquire.

Another probable reason for the VAS pulse only being used medically to a very limited extent is that there has been incomplete knowledge as to the relationship of the VAS pulse to physiological conditions of a particular body. One of the surprising things that has, however, been established about the VAS pulse is that this particular pulse is responsive to a variety of different stimuluses. Thus, it has been recognized that variations will occur in the VAS pulse as a result of stimulation of the auricle or other body parts as, for example, by subjecting the auricle or such other parts to different types of physical manipulation or different types of radiation.

By comparing such variations in the presence of a stimulation not having a known reaction on a particular body with a stimulation having a known or established reaction or causing a particular type of variation, it is possible to utilize the VAS pulse as a means of predicting body reactions to particular stimulations. This is so little understood, that normally variations in the VAS pulse will not be utilized for medical treatment, diagnosis or treatment purposes as, for example, in determining how the body will react to a specific form of treatment until there have been further developments in the field of auricular medicine approving of the safety and effectiveness of the use of the VAS pulse for medical purposes.

This however, is no reason why the VAS pulse cannot be satisfactorily utilized in making physiological measurements which can be of value for non-medical purposes in measuring the body's responses to various stimuluses. Thus, it is possible to utilize the VAS pulse in manners analogous to the manners in which various different body responses are measured in devices such as common lie detectors and the like. The VAS pulse can be utilized for other physiological purposes such as in studying the reaction of a living body having an arteriovascular circulatory system to specific aspects of the changing ambient world.

In the use of the VAS pulse for such physiological purposes in accordance with the findings of Dr. Nogier, several problems have been encountered. One of these concerns the comparatively limited amount of information or data which can be obtained from the pulse at the specific—but not identified—location indicated in the preceding discussion. Another concerns the fact that such information or data attained at this location does not apparently specifically indicate body conditions which may be significant in connection with a physiological evaluation at various other specific locations or regions of the body, or in certain organs of the body. In time, it may be established that these same measurements are legally and universally acceptable for medical uses. It will be apparent that this latter will depend upon various national laws.

SUMMARY OF THE INVENTION

The invention is intended to provide both a method and apparatus for the purpose of improving the amount and the reliability of the information relative to a living body having an arteriovascular circulatory system which can be obtained by measuring or monitoring the VAS pulse. The invention is also intended to provide both a method and apparatus for obtaining related information at a number of locations which are adjacent to but spaced from the specific location where the VAS pulse can be measured or monitored. The related information obtained at any such another location can be used alone but is preferably utilized in conjunction with other information of the same type obtained at other locations—including that obtained by monitoring or measuring the VAS pulse—for the purpose of facilitating an understanding of the operation of the body.

All of the information indicated in the preceding discussion is considered to be both important and valuable in connection with a physiological understanding of the reactions of and performance of a human or other animal body. Such information is also considered to be significant as indicating the probable future or continued performance of such a body unless the body is subjected to a stimulus which will change such performance. This information is also considered to be important and valuable as indicating how a particular body will probably react when subjected to any such stimulus or will probably react when subjected to several such stimuli.

The term "stimulus" as used in the preceding discussion is used in the broadest possible sense or connotation. Any item which is capable of causing a psychological effect or any sort of physical force can operate so as to stimulate the body in one manner or another. The mind itself is such an item. Further, the body will normally be stimulated by all sorts of extraneous and miscellaneous "forces" of a non-physical character. Many of the latter are probably not completely understood.

Thus, the information achieved in accordance with this invention will vary depending upon whether a part of a body has been subjected to a light of a specific color. It will apparently also vary depending upon the thought patterns of an individual involved. In short, virtually anything can be considered as a stimulus capable of causing physiological reaction. Further, frequently the proximity of the body to a specific thing will cause the same reaction as the thing itself. Normally, items of similar characteristics will cause the same type of change in the information achieved. Further, the mental state or condition of a person will also cause a variation in the nature of the information achieved in accordance with this invention.

It is believed that it will be apparent from the preceding that the information which can be obtained in accordance with the present invention can be quite valuable in understanding and studying the physiological aspects of the performance of a living body. Because of the interrelationships between physiology and medicine, it will be apparent that much of the information obtained in accordance with this invention will have direct known or unknown medical significance. Whether or not any such information should be utilized in medical practice will depend upon considerations which are unimportant to an understanding of the principles or concepts of the present invention.

It is also believed it will be apparent from the preceding and from the subsequent portions of this specification that the invention is intended to provide a process for use in making measurements on a living body having an arteriovascular circulatory system which comprises immobilizing part of the body in which an artery extends substantially linearly and adjacent to and substantially parallel with the skin, locating both a radiation source and detection means adjacent to a specific location along the length of said artery which has been established as normally being capable of reflecting at least some incident radiation in an amount having physiological significance, said radiation source and detection means being located in a position such that radiation from said source means will be modified as a result of contact with the body in reaching said detection means, operating said radiation source and detection means so that radiation emitted by said source means is modified in reaching said detection means and is used to produce a signal at said detection means which is indicative of at least one physiological function.

The invention is further intended to provide an apparatus for use in making measurements on a living body having an arteriovascular circulatory system which comprises a support means for engaging a part of the body adjacent to a location in the body where a length of an artery extends substantially linearly and is adjacent to and generally parallel with the surface of the skin so as to substantially immobilize said part without interfering with the circulation of blood within said artery, said support means being shaped so as to include an opening means adjacent to said length of said artery, radiation source and detection means for use in making measurements by sending out radiation from said source means and by measuring radiation reaching said detection means, holder means for holding said radiation source and detection means located adjacent to said opening means, said holder means supporting said radiation source and detection means adjacent to said opening means, positioning means for moving said holder means into any of a series of successive locations along said length of said artery which have been established as normally being capable of transmitting at least some radiation in an amount having physiological significance from a radiation source, said holder means and said positioning means serving to hold said radiation source and detection means in each of said locations so that some radiation from said source means will traverse a part of said body and will be detected by said detection means.

From a careful consideration of the remainder of this specification, it will be apparent that the subject matter of the present invention has a number of somewhat unusual or surprising aspects and at times becomes quite involved. Apparently because of variations in human metabolisms and other factors, the present invention cannot always be utilized satisfactorily with all persons. It is assumed that this is also the case in connection with various types of animals. As subsequently indicated, in certain instances the effectiveness of the present invention in providing information of a psysiological significance is better than in others. These factors are not to be taken as indicating that the invention lacks utility. In this connection, it should be noted that most drugs and many items of diagnostic and treatment equipment are considered to have utility even though they are not 100% effective.

BRIEF DESCRIPTION OF THE DRAWINGS

Because of the inherent character of the present invention, it is considered that it is best more fully described with reference to the accompanying drawings in which:

FIG. 1 is an isometric view of a presently preferred embodiment of an apparatus for use in making measurements generally along the human wrist along the radial artery;

FIG. 2 is a partial cross sectional view on an enlarged scale taken at line 2—2 of FIG. 1;

Figure 3:
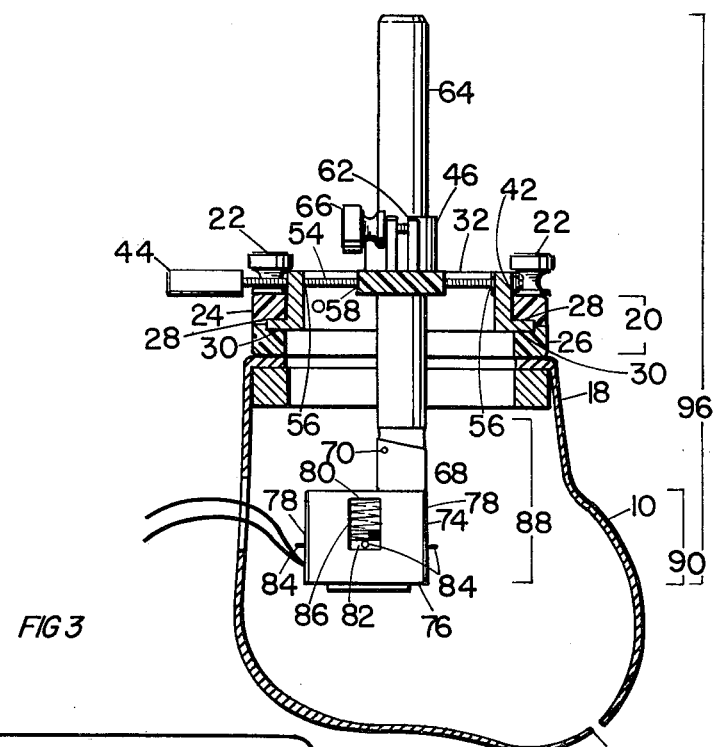
FIG. 3 is a partial cross sectional view on an enlarged scale taken at line 3—3 of FIG. 1.

The invention is not to be considered as being limited to an apparatus as illustrated in the drawings or to a process in which this equipment is used to obtain measurements inasmuch as the invention embodies certain essentially intangible concepts or principles as are set forth and defined in the claims forming a part of this specification. It is believed that those familiar with the measurement of various physiological aspects of the performance of a body through the use of electronics will have little or no difficulty in developing a number of different items of equipment which are capable of utilizing these same concepts or principles through the use or exercise of routine skill in the field of such measurements. Further, it is believed that such individuals will have no difficulty in adapting the concepts of the present invention so that the measurements obtained are processed in accordance with known techniques by computers to obtain non-obvious results as are specified in the remainder of this specification.

DETAILED DESCRIPTION

It is considered necessary to immobilize a portion of a body where a length of an artery extends substantially linearly and is adjacent to and generally parallel with the surface of the skin as a prelude to the subsequent steps involved in practicing the present invention in making measurements. Further, an area of the body should be chosen where the skin and the limited other tissue overlying the artery is comparatively flexible, elastic and resilient in character so as to be capable of deforming in response to the flow in the artery caused by the normal operation of the heart and the "action" of the sympathetic, parasympathetic and autonomic nervous system. This matter of the resiliency and pliability of the skin is not particularly important when a form of radiation is to be used which readily penetrates the skin but is important when a form of radiation is used, such as infrared radiation of a frequency which is "blocked" by the surface of the skin which will not significantly penetrate the skin.

The part of the body which is immobilized is essentially a matter of choice. In practicing the invention with the human body, it is preferred to immobilize the wrist, the adjacent portion of the hand and the principle portion of the forearm of a human. This is because these portions of the human body are normally reasonably exposed so as to be readily accessible and because the radial artery is located immediately adjacent to the surface of the wrist and extends substantially linearly, generally parallel to the skin along the wrist. When the invention is utilized with other than humans, it is considered that other portions of a body will be preferred for use in making measurements in practicing this invention.

A presently preferred manner of achieving this manner of immobilization in the human wrist is indicated in FIG. 1. Here there is shown an elongated, hollow, split-sleeve like gauntlet 10 formed of a comparatively rigid, self supporting material which has a limited, resilient flexibility. This resiliency becomes important in locating the gauntlet 10 in an operative location in which the gauntlet 10 surrounds the portion of a hand generally adjacent to the wrist including a part of the thumb, the wrist itself and a portion of the forearm generally adjacent to the wrist.

This gauntlet 10 is provided with an elongated slit 12 which permits it to be sprung apart so as to be fitted in an operative location as noted. Known or conventional closure straps 14 are used on the gauntlet so as to extend across the slit 12 for the purpose of securing the gauntlet 10 together as a substantially rigid, integral unit. When in place, the gauntlet 10 will immobilize substantially enough of the human body next to the wrist so that an elongated, rectilinear opening 16 on the gauntlet 10 is generally adjacent to and opposite that portion of the wrist where the radial artery is located.

Care should be taken to utilize a gauntlet 10 which is sufficiently large internally so as not to cause discomfort but which is not so large as to be ineffective at preventing inadvertent muscle movement in the vicinity of the opening 12. This is because such movement might be confused with movement of the radial artery. It is understood that the invention does not require the use of a gauntlet corresponding to the gauntlet 10. This gauntlet 10 is merely a support or support means (not separately numbered); any other reasonably equivalent expedient for temporarily immobilizing a part of the body can be substituted for it. Any such substituted expedient should be capable of holding various parts as subsequently indicated or should be employed with another support such as a frame (not shown) for holding these parts.

Preferably, but not necessarily, this opening 16 will be surrounded by an upstanding flange 18 forming a part of the gauntlet 10. This flange 18 is preferred because it provides room to accommodate various operative parts as hereinafter described. Preferably, a rectilinear frame 20 is mounted on the flange 18 so as to surround the opening 16 through the use of corner thumb screws 22. This frame 20 consists of upper and lower frame parts 24 and 26 which are shaped so as to define between them two parallel linear grooves 28 which are directed towards one another.

These grooves 28 retain flanges 30 on a squarish sub-frame 32 in such a manner that the sub-frame 32 is capable of movement generally between the ends 34 of the frame 20. An elongated threaded shaft 36 extends through aligned bearing openings 38 in the ends 34 of the frame 20 and is threaded through other aligned openings 40 in the sub-frame 32. This shaft 38 is held in position relative to the frame 20 through the use of conventional shaft collars 42 and is provided with a small handle 44 which is intended to facilitate its being turned. It will be apparent that when the handle 44 is turned the sub-frame 32 will be moved generally between the ends 34.

The sub-frame 34 serves to support a small carriage 46 so that it can be moved back and forth perpendicular to a line drawn between the ends 34. This carriage 46 is in part supported by a pinlike guide shaft 48 press fitted within holes 50 in the sub-frame 32. This shaft 48 fits closely through the interior of another hole 52 in the carriage 46 in such a manner as to accommodate movement. The carriage 46 is also supported by another threaded shaft 54 which extends through other holes 56 in the sub-frame 32. This shaft 54 extends parallel to the shaft 48; it is held in place by shaft collars 42 and carries a handle 44 which can be utilized in turning the shaft 54. When the handle 44 associated with the sub-frame 32 is turned, engagement between the shaft 54 and a threaded hole 58 in the carriage 46 will move this carriage 46 back and forth.

It will be apparent that the frame 22 and the associated structure in general mounted upon it constitutes what may be referred to as an x-y table 60 of such a character that the carriage 46 may be moved linearly in the directions of two different axes located perpendicular to one another. Of course, motion which is not in alignment with one of such axis can be achieved by concurrently manipulating both of the handles 44. If desired, other types of structures may be utilized in lieu of this x-y table 60. Because of its function this table 60 may be referred to as a coordinate table or means or as a means for moving the carriage 46 in a coordinate system. This particular x-y table 60 is considered desirable because it is possible to substitute for the handles 44 small motors (not shown) which will automatically move the frame 20 and 32 in response to appropriate signals and because it is relatively easy to provide appropriate circuitry to operate such meters.

The carriage 46 is provided with a small split collar-like holder 62 which is adapted to be secured around the exterior of a rod 64 through the use of a conventional thumb screw 66. This rod 64 carries a downwardly directed extension 68 which is secured by a pin 70 within a slot 72 in a generally rectilinear housing 74. It will be noted that the rod 64 and the housing 74 are shaped so as to permit limited movement or pivoting about the pin 70 in a single plane between the housing 74 and the rod 64. This housing 74 has an open bottom 76. It also has end slots 78 and side openings or slots 80. Generally within the housing 74 there is located a small plate 82 carrying pins 84 which fit within the slots 78 and 80. A small coil spring 86 within the housing 74 normally biases the plate 82 so that the pins 84 are against the bottoms of the slots 78 and 80. With this construction, however, the plate 82 is capable of being moved generally towards the rod 64 by the application of pressure.

This entire structure involving the housing 74 and the manner in which the housing 74 is secured to the rod 64 may be referred to as constituting a species or form of gimbal 88 which constantly holds the plate 82 in such a manner as to accommodate various types of movement of the plate 82 as are encountered during the use of the described structure. In effect, the housing 74 and the associated structure can be considered as a holder 90 or holder means for use in holding a radiation source 92 and a radiation detector 94. The entire structure constituting the x-y table 60 and the collar 62 permitting adjustment of the structures 92 and 94 along a z axis relative to the table 60 constitutes a type of positioning structure 96 or means which may be utilized to manipulate or move both the holder 90 and the radiation source and detection structures 92 and 94, respectively, held by it along perpendicular x, y and z axes during the use as measurements are taken in accordance with this invention.

Both the radiation source and the radiation detector 92 and 94 employed should, of course, be capable of emitting and detecting the same type of radiation. The nature of such radiation may be varied within comparatively wide limits. At the present time, it is preferred to utilize as the source and the detector 92 and 94, respectfully, ultrasonic send and receive "heads" or transducers which will emit an ultrasonic signal in a range of about 20 mHz at a repetition rate of about 1 pulse or "burst" per 1/2,500 of a second of a duration of about 600 nanoseconds. The power used to drive the head 92 is preferably the minimum which will provide a reflected signal at the detector 94.

It is not to be assumed from this that the invention is only of significance in connection with radiation of the particular type or frequency specified. Effective results can be achieved in accordance with this invention utilizing either continuous or intermittent ultrasonic vibrations of a wide variety of different frequencies. Any such ultrasonic radiation used should be of a power level inadequate to noticeably act as a stimulus causing any physiological reaction but adequate to obtain a reflected signal from generally within the interior of the artery toward which the source 92 and detector 94 are directed; preferably a reflective signal which is primarily off of the interior wall of the artery remote from the skin of an individual and, of course, remote from the radiation source and detectors 92 and 94 used.

It is also possible to utilize as a radiation source 92 a source of infrared radiation or near infrared radiation which will tend to penetrate the skin adjacent to an artery to at least a sufficient degree so that some reflected infrared radiation received back by the radiation detector 94 will reflect "conditions" generally within and/or movement associated with the artery used in making measurements. Infrared radiation having a wave length of 902 and 2240 nanometers is considered to be usable in making measurements in accordance with the present invention. On the other hand, infrared radiation having a wave length of about 500 nanometers is not considered to be particularly desirable for use with the present invention because any signal received back by a detector 94 will be primarily based upon skin movement and skin resilience and will not significantly reflect the condition and/or movement of an artery such as the radial artery.

It is theorized that other types of radiation may be utilized with the present invention. Thus, there is theoretically no reason as to why an appropriate radio frequency signal could not be employed for at least some measurement purposes. Care must be taken, however, that the radiation used will be capable of permeating at least as far as the artery and preferably within the artery and is capable of being reflected back at least in part towards the detector 90 employed without causing any detrimental or undesirable effects. Thus, for example, it would be inappropriate to utilize a radiation source such as either radio frequency or infrared radiation at a power level which might cause noticeably localized heating. Apart from the possible detrimental character of such heating, such heating is objectionable as in and of itself constituting a form of a stimulus which would affect the validity of any measurement made as indicated in this specification.

In making measurements in accordance with the invention, it is first necessary to position a gauntlet 10 or whatever other equivalent structure may be employed instead of a gauntlet 10 in an operative position to immobilize either the human wrist or any other part or limb of a body so as to effectively immobilize that part of the body adjacent to the artery where measurements are to be made. With the gauntlet 10, this artery will, of course, be the radial artery. Next, the structure employed is normally manipulated so that the source and detector 92 and 94, respectively, are located relative to the artery in a location such that they will be subjected to maximum physical movement of the artery. In effect, this means that the source and detector 92 and 94 will be directly above the artery so that any measurements obtained will be based upon the artery and/or phenomena associated with the artery and will not primarily relate to other occurrences within the body.

In addition, the source and detector 92 and 94 normally will be concurrently "coupled" to the skin of the body in such a manner as to provide for the effective transmission of radiation when the radiation used is of such a character that this is reasonably desirably or required. This is primarily needed in connection with ultrasonic radiation. Such coupling normally will merely involve coating the skin in the general area where measurements are to be made with an appropriate, conventional, viscous composition capable of transmitting ultrasonic vibrations such as, for example, is used in connection with body scanning. If the radiation used is of a radio frequency, a similar composition of an electrolyte type is preferably employed. These electrolyte compositions are commonly utilized in connection with electrodes in taking electrocardiograms and the like.

Normally, it will be convenient and desireable at this point to "ground" the body upon which the measurements are to be made. If desired, however, such grounding can be performed prior to locating the radiation source and detector 92 and 94, respectively, at a location corresponding to the maximum physical movement of an artery. This grounding is not required in all cases in order to obtain "effective" measurements or measurements of a desired character. It is, however, considered to be very highly desirable to ground any body upon which measurements are made in accordance with this invention since grounding very materially increases the chances of any measurements being made being of a desired character capable of being utilized for purposes as indicated earlier in this specification.

The grounding used may merely consist of grounding any single part of a body upon which measurements are to be made to the ground in the conventional manner in which any piece of electrical equipment is grounded. This can consist of merely placing a conductor in contact with that part of the body and connecting the conductor to a water pipe or any other metal object extending into the ground. The effectiveness of this can be improved by utilizing an electrolyte composition as previously noted to connect the conductor with the body.

It is considered that improved results in the form of more consistently desirable measurements are achieved by varying this grounding procedure so as to utilize as conductors comparatively large metal objects 98 which are in contact with the limbs of a body upon which the measurements are to be made. It does not appear to be particularly significant as to whether or not the particular limb upon which measurements are to be taken is grounded or not. In general, such grounding connections to the body should be made as reasonably close to the extremity of a limb as conveniently possible. Apparently, best results are achieved when such grounding is in an area such as the palm of the hand or the sole of the feet where there is adequate area for contact between the body and the conductor and where there are significant nerves present. Thus, the various limbs can be grounded through the use of copper rods or plates held in one or both hands of a human and against the feet of the person involved.

Apparently, it is best to ground each limb of the body separately and not to connect them to a grounding connection 100 such as a water pipe utilizing a common conductor. This is believed to relate to the fact that various different body "signals" such as, for example, the pulse and various nerve reactions are believed to "reach" various extremities of the body at slightly different time periods. If there was a concurrent grounding of all limbs to a common conductor, there is a possiblity that the conductor 102 used for grounding purposes serves to convey at least a vestige of a signal from one limb to another and this might tend to effect the results achieved.

Although the grounding described in the preceding is considered to be reasonably desirable and effective, it is believed that preferred results are achieved by grounding each limb through the use of a capacitor 104. This is indicated in a diagrammatic manner in FIG. 4 of the drawings. At the present time, the capacitance value of any capacitor used appears to be essentially a matter of choice which is best determined on a purely empirical basis on the basis of the shapes and configurations of curves which are obtained as the result of measurements as subsequently indicated in this specification. It is believed that some will prefer the use of variable capacitors in the conductors employed in grounding limbs of the body. It is believed that others will prefer the use of capacitors employing dielectrics exhibiting limited semi-conductive or similar properties.

It is considered that further experimentation of a routine character will establish the optimum way that any particular type of body should be grounded and that this will depend upon the nature of the body involved. Thus, for example, it is considered that an entirely different grounding procedure will be required in connection with a horse than is required with a human.

Normally, the next step involved in practicing the invention will require the location of the source and detector 92 and 94, respectively, in what is referred to as the VAS point or location along an artery. This point or location along the radial artery on the human body will be approximately 4.2 mm towards (proximal) the trunk of the body from the radial styroid at the wrist. This particular point or location is quite critical to certain concepts of the present invention and, of course, to obtaining satisfactory measurements in practicing the present invention. Inasmuch as the VAS point or location is recognized in medical literature, it is not considered necessary to extensively discuss the identification of this particular point in the artery in this discussion.

As a practical matter, a VAS point or location is neither from a technical standpoint. A VAS point or location is really that disclike volume in a plane approximately 3 mm thick extending perpendicular to the length of an artery which is completely enclosed by the outer periphery of the artery within which the physical "condition" of the wall of the artery is more indicative of various aspects of the operation of a body than any other adjacent similar area or volume located along the length of the artery. This term "condition" employed in this definition is intended to designate a number of different physical characteristics and properties such as resiliency, elasticity, density, pliability and the like which contribute towards the way that any specific composition reacts to the application of energy in either the form of radiation or the form of a more conventional type of physical force.

At a VAS area or location, the physical "condition" of the walls of the artery may be monitored or measured to a very limited extent by applying a conventional physical force to the artery so as to obtain a "signal" in response to the applied force which is indicative of such condition. In the simplest case, the force consists of a moderate amount of pressure applied as, for example, by the tip of the thumb by a person who is "taking" what may be referred to as a "VAS pulse" at a VAS area or location. In this particular case, the "feel" at the part of the thumb used to take the pulse is indicative of the physical condition and of the normal blood flow in the artery.

The procedure involved here is referred to as taking the VAS pulse inasmuch as inherently the feeling at the thumb of the person taking the VAS pulse will reflect the variations in the artery at a VAS area or location caused by the normal flow of blood in the artery. However, when a VAS pulse is taken, the intent is to obtain an indication of the "reactions" of the artery within a VAS volume or area which are essentially independent of the actual blood flow in the artery except, perhaps, to the limited extent that such blood flow is indicative of various physical properties of the walls of the artery as are noted in the preceding discussion. In other words, when normally taken the VAS pulse may be considered as the signal in the form of a feeling which is obtained by the person taking the pulse which such person mentally processes so as to neglect that aspect of such feeling caused by the actual pulse in the VAS area or location.

In the preceding definition of the VAS point or location, it was indicated that within the VAS area the wall of the artery is more indicative of various aspects of the operation of the body than other adjacent areas or volumes. The term "indicative" as used here is intended to indicate the relative ease with which an indication of the physical condition of the wall of the artery can be obtained. When the VAS pulse is taken manually, as indicated in the preceding, this pulse will be more pronounced and more easily discerned at a VAS point or area than at other points along an artery.

The "responsiveness" of the wall of the artery in a VAS area or location, as indicating one or more body conditions, is apparently not confined to a responsiveness as a result of the application of any particular type or form of radiation or physical force. Within a VAS area along the length of an artery a signal from an ultrasonic transducer will either be transmitted to the other side of the artery or reflected back by the walls of the artery which is of greater amplitude than the signal which will be transmitted or reflected at another adjacent location. Similarly, at a VAS point or location, an infrared radiation capable of penetrating the skin to at least a degree will normally be reflected back to a greater extent than at any other location along the length of an artery.

All of these factors are considered important in recognizing when the physical structures previously described are manipulated so that the source and detector 92 and 94, respectively, are located at or about the VAS point or location along an artery. This is considered important because normally the VAS point or location will serve as a reference point for other subsequently made measurements serving to monitor the "condition" of the artery at various areas along the length of the artery. Further, the VAS point or area is important because frequently a particular type of radiation used with the source and detector 92 and 94, respectively, will only be productive of a reflected signal reaching the detector 94 having significance in physiological measurements at or about the VAS point.

It has previously been recognized that a VAS point will reoccur at periodic intervals of a uniform length along the length of an artery such as the radial artery. It has also been recognized that this length will vary somewhat depending upon the diastolic blood pressure of a human and—presumably, any other animal. Thus, in the human body there will be a series of VAS volumes which are normally located in planes which will be uniformly spaced from one another by distances of from about 7.8 to about 11.2 mm in accordance with the diastolic blood pressure at a particular time. In general, the higher the blood pressure, the greater the spacing.

Because of the fact that the VAS areas reoccur at such intervals it is possible to consider the VAS pulse as a form of wave phenomena. As a consequence of this it is possible to consider the VAS pulse from a mathematical standpoint in order to obtain a coefficient which corresponds to the resiliency of the wall of an artery. Such a coefficient is in and of itself of interest inasmuch as it has physiological significance. However, such a coefficient does not indicate or suggest all of the information which may be obtained from the VAS pulse or which may be obtained at a VAS point or location.

This information reflects the fact that the physical characteristics in the artery of a living body are not static but constantly change in accordance with the operation of the body. As a result of experience, it is believed that it is reasonably established that the VAS pulse at a VAS point, area or volume reflects a complex function or integral relating the operations of the sympathetic and parasympathetic nervous systems which constitute the autonomic nervous system of the body. Both of these systems in one manner or another influence commonly measured physical properties and characteristics of the wall of the artery in a VAS area and in other areas or volumes between VAS area.

The manner in which this is accomplished probably is not a simple matter but instead must concern all sorts of variables related to the operation of the body. Thus, for example, the physical characteristics of various cells at various locations within the wall of an artery at a VAS location will undoubtedly be dependent upon a number of factors such as cell concentrations, relative hydration, applied pressure due to the pulse and due to muscle tension and so on. Fortunately, an understanding of the present invention does not require an understanding of all of these factors.

This invention, however, is important in that it relates a number of matters of physiological importance to such factors only in the indirect sense that such factors influence radiation directed toward an artery at a VAS location being reflected, transmitted or absorbed. By measuring the amplitude of a signal obtained by directing radiation at an artery at a VAS location and received by a detector located so as to either receive such of the radiation as passes through the artery or is reflected back by the artery at or about a VAS location, it is possible to obtain information which will enable a plot to be made of the amplitude of such signal against time. The plot will appear as a curve having characteristic peaks which are primarily indicative of certain specific aspects of body performance, such as, for example, certain specific aspects of the performance of the heart, the liver and so on.

This is best illustrated with reference to FIG. 6 of the drawings illustrating a curve which is obtained by plotting the amplitude of an ultrasonic signal received back at a detector 94 from a radiation source or sending head 92 used to send and receive an ultrasonic signal as specifically indicated in the preceding discussion. This curve in FIG. 6 and all other curves shown in the drawing are not actual curves but are intended to substantially illustrate the character of actual curves. This is because of problems in adequately duplicating curves as are observed on the screen of an oscilloscope to the standards of drawings as are employed for patent purposes. In obtaining any curve such as the curve shown in FIG. 6 an appropriate electronic package 106 is used to operate the radiation source 92 and to process the signals received at the detector 94. This "package" 96 will normally be used to display a curve corresponding to the curve shown in FIG. 6 on an oscilloscope tube 108. If desired, this package 96 may be utilized to provide a reading on a meter 110 indicating the area underneath a particular length of the curve.

Figure 6:
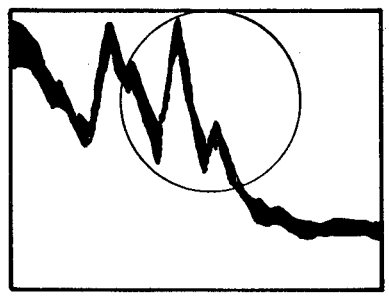
FIG. 6 shows a curve approximately corresponding to a curve obtained by electronically processing measurements taken, as subsequently indicated, at a location corresponding to the VAS point.

In order to obtain this particular so-called VAS curve shown in FIG. 6, a source and detector 92 and 94 were located as close to a VAS area in the radial artery as reasonably possible through manipulation of the physical structure previously described in a location in which the axes of the source and detectors 92 and 94 were directed substantially towards the same point on the surface of the inner wall of the artery at a VAS location on the side of this artery remote from the source and detector 92 and 94 in a plane perpendicular to the artery passing through what was referred to in the preceding as the VAS volume. These axes could have been located in a plane passing through the center of the artery.

In order to obtain effective results, the source and detector 92 and 94 were located at an angle relative to the artery such that a significant amount of ultrasonic radiation from the source 92 was reflected back to the detector 94. Preferably, this angle is from about 14.3° to about 14.5° in order to obtain as strong a reflected signal as reasonably possible. Broadly, however, any angle from about 14° to about 14.8° can be employed although the closer the angle to the preferred range the better. Surprisingly, these same values apply when other types of radiation as discussed are used.

These peaks in a so-called VAS curve as illustrated in FIG. 6 are considered to all have a degree of physiological significance. Further, these peaks along a VAS curve provide a convenient way of recognizing whether or not a radiation source and a detector 92 and 94 respectively are located at a so-called VAS point since these peaks will all be in roughly the same location along a VAS curve. If desired, a computer may be used for comparison purposes in order to compare the shape of a particular curve with a standard VAS curve for the purpose of verifying peaks at the same location along the time axis in order to verify that in fact a VAS curve is being obtained.

Figure 7:
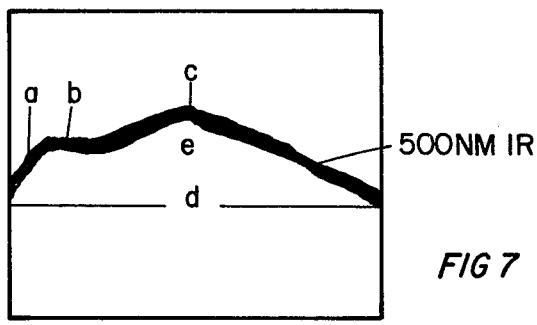
FIG. 7 approximately shows the so-called "VAS curve" obtained from a portion of the curve at the VAS location marked with a circle by "processing" the signal electronically and the approximate shape of portions of other similar curves obtained with different radiation.

The significance of certain of these peaks and areas adjacent to them and underneath them is a matter of paramount importance to the present invention. This is best illustrated by referring to a portion of a so-called VAS curve as illustrated in FIG. 7. This portion of a VAS curve corresponds to that part of the complete curve illustrated generally within the circle in FIG. 6 of the drawings. The particular partial curve shown in FIG. 7 is the result of processing that portion of the VAS curve designated in FIG. 6 electronically so as to expand it to a sufficient degree so that the various features or aspects of the curve may be studied and examined without significant difficulty.

On the basis of observations it is considered possible to utilize that portion of the curve from FIG. 6 which is illustrated in FIG. 7 in order to obtain information of a physiological value in determining the body's reaction to virtually any type of stimulus. Normally an indication as to whether or not a particular stimulus will or will not be beneficial to a body can be determined by whether or not the area "e" will increase or decrease as such stimulus is applied to or otherwise used in connection with the body upon which measurements are being made. The nature of a curve such as that portion of the curve illustrated in FIG. 7 will also vary depending upon various other factors of physiological significance. As a result of the latter the present invention is considered to have particular utility in connection with stress analysis and in connection with so-called "lie detecting" procedures.

In the areas along all of the artery between the VAS points or nodes it is possible to obtain a series of curves reasonably corresponding to a VAS curve as indicated in FIG. 6, but differing from such a VAS curve as to the specific peaks which are to be expected at any precise location. Such curves can be easily obtained by manipulating the physical structure described in the preceding or another reasonably related structure so as to move the radiation source and detector 92 and 94, respectively, generally along an artery. This movement is inherently simple with the structure previously described and is facilitated by virtue of the fact that the structure described will normally be located so that only a simple shaft has to be rotated in order to move the source and detector 92 and 94. The movement described here may easily be carried out automatically through the use of motors as indicated in the preceding.

Figure 5:
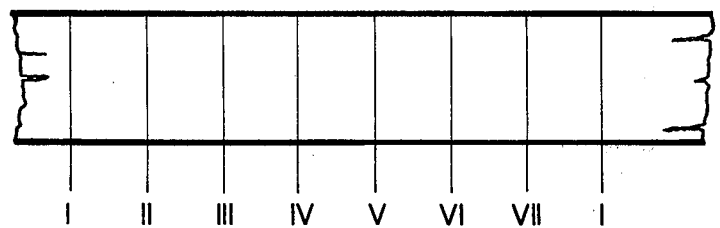
FIG. 5 is a diagrammatic cross sectional view of a length of the radial artery showing the so-called VAS area or location (also sometimes referred to as point) and various so-called "windows" which are somewhat related to this VAS area.

As a result of experimental work six different so-called "windows", each corresponding to a VAS disk-like volume as described in the preceding have been located and at least partially identified or catalogued between adjacent VAS locations. As a means of identifying such areas it is considered desirable to designate a VAS location or area utilizing the Roman numeral I and to designate such subsequent volumes by Roman numerals II through VII as shown in FIG. 5. In effect a VAS area or location may be considered as a "window" with this method of identification. Each of the various windows noted in effect constitutes a disk-like volume approximately 0.3 mm thick extending perpendicular to the center of the artery and bounded on the exterior by the outer wall of the artery.

These particular points or locations designated by the Roman numerals II through VII are significant primarily in that the peaks of curves corresponding to a VAS curve taken at each of these locations have been determined on the basis of experimental observation to always recur at substantially the same locations and in that at least some of these peaks at these locations have been determined by observation to have significance in connection with the operation of certain parts of the body, such as, for example, the sympathetic and parasympathetic nervous systems, the heart, the kidneys and so on. It is believed that various slopes, areas and amplitudes of curves as are obtained at any location along the length of an artery between VAS points will have significance at least partially corresponding to the significance of various aspects of a VAS curve.

The recurrence of the peaks of curves at repetitive locations on curves taken at the same windows and the fact that curves taken at different windows between two VAS points wil differ makes it possible for a computer to compare the curve obtained at any time between two VAS points with an average or pattern type curve obtained at a specific window to determine whether or not the source and detector 92 and 94 used are or are not in a proper location corresponding to this specific window. Similarly either visually or by computer as a result of comparison with a so-called standard curve it is possible to determine what aspects of a body are "performing" in a desired manner and what aspects of a body are not.

It is not to be assumed from the preceding that the shape of a curve obtained at any VAS point or at any specific window will be the same with one type of radiation as it will be with another type of radiation. It has been determined that the shape of the curve obtained at any specific location or area will vary in accordance with the specific character of the radation used.

I claim:

1. An apparatus for use in making measurements on a living body having an arteriovascular circulatory system which comprises:
   a support means for engaging a part of the body adjacent to a location in the body where a length of any artery extends substantially linearly and is adjacent to and generally parallel with the surface of the skin so as to substantially immobilize said part without interfering with the circulation of blood within said artery, said support means being shaped so as to include an opening means adjacent to said length of said artery,
   a radiation source means and a radiation detection means for use in making measurements by sending out radiation from said source means and by measuring radiation reaching said detection means,
   holder means for holding said radiation source and detection means located in a location adjacent to said opening means, said holder means supporting said radiation source and detection means adjacent to said opening means,
   positioning means for moving said holder means and said radiation source and detection means relative to said support means in a coordinate system into any of a series of locations along said length of said artery which have been established as normally being capable of transmitting at least some radiation in an amount having physiological significance from a radiation source, said positioning means being held on said said support means,
   said holder means and said positioning means serving to hold both said radiation source means and radiation detection means at a specific measurement location so that as said apparatus is used at such a location some radiation from said radiation source means will traverse a part of said body and will be detected by said radiation detection means.

2. An apparatus as claimed in claim 1 wherein:
   said support means comprises a gauntlet like sleeve adapted to fit closely around a portion of a limb of said body.

3. An apparatus as claimed in claim 1 wherein:
   said support means comprises a gauntlet like sleeve adapted to fit closely around the forearm, the wrist and the portion of the hand adjacent to the wrist of a human body, and
   said opening means comprises an opening to said gauntlet located adjacent to the portion of said sleeve adjacent to the human wrist where the radial artery is located.

4. An apparatus as claimed in claim 1 wherein:
   said holder means and said positioning means hold said radiation source and detection means so that in each of said locations a signal from said source means will be directed towards an internal area within said artery and will be reflected back from said area towards said detection means.

5. An apparatus as claimed in claim 4 wherein:
   said areas at said locations each corresponds to a portion of said artery located generally in a plane extending perpendicular to said artery.

6. An apparatus as claimed in claim 5 wherein:
   both said radiation source and detection means have axes and both of said axes are directed substantially towards the same point on the interior of the wall of the artery in each of said locations,
   said source and said detection means also being located on the opposite side of said artery from said point at an angle relative to said artery such that radiation from said source means will be reflected back to said detection means in each of said locations.

7. An apparatus as claimed in claim 6 wherein:
   said radiation source means is separate from said radiation detection means, and
   the axis of said source means and the axis of said detection means are located at substantially the same angle relative to a plane extending perpendicular to said artery in each of said locations,
   said angle is an angle of from about 14° to about 14.8°.

8. An apparatus as claimed in claim 7 wherein:
   said angle is an angle of from about 14.3° to about 14.5°.

9. An apparatus as claimed in claim 1 wherein:
   said positioning means comprises an x-y table means supporting said holder means so that said holder means and said radiation source and detection means may be moved along the length of said artery to said successive locations.

10. An apparatus as claimed in claim 1 including:
    grounding means for grounding the portions of said body remote from said part of said body through capacitor means.

11. An apparatus as claimed in claim 1, 2 or 4 wherein:
    said areas at said locations each correspond to a portion of said artery located generally in a plane extending perpendicular to said artery,
    both said radiation source and detection means have axes and both of said axes are directed substantially towards the same point on the inter-wall of the artery in each of said locations,
    said source and said detection means also being located on the opposite side of said artery from said point at an angle relative to said artery such that radiation from said source means will be reflected back to said detection means in each of said locations,
    said radiation source means is separate from said radiation detection means,
    the axis of said source means and the axis of said detection means are located at substantially the same angle relative to a plane extending perpendicular to said artery in each of said locations,
    said angle is an angle of from about 14.3° to 14.5°, and
    said radiation source means is a means for emitting infrared radiation and said radiation detection means is a means for detecting infrared radiation so as to provide an output signal in accordance with the radiation received by it.

12. An apparatus as claimed in claim 11 including:
    grounding means for grounding the limbs of said body remote from the limb of the body on which said part of said body is located through capacitor means.

13. An apparatus as claimed in 1 wherein:
    said areas at said locations each correspond to a portion of said artery located generally in a plane extending perpendicular to said artery,
    both said radiation source and detection means have axes and both of said axes are directed substantially towards the same point on the inter-wall of the artery in each of said locations,
    said source and said detection means also being located on the opposite side of said artery from said point at an angle relative to said artery such that radiation from said source means will be reflected back to said detection means in each of said locations, said radiation source means is separate from said radiation detection means, the axis of said source means and the axis of said detection means are located at substantially the same angle relative to a plane extending perpendicular to said artery in each of said locations, said angle is an angle from about 14.3° to 14.5°, and said radiation source means is capable of continuously emitting ultrasonic radiation and said radiation detection means is capable of providing a continuous signal varying an amplitude in accordance with the ultrasonic radiation received by it.

14. An apparatus as claimed in claim 13 including:

grounding means for grounding the limbs of said body remote from the limb of the body on which said part of said body is located through capacitor means.

15. An apparatus as claimed in claim 1 wherein:

said areas at said locations each correspond to a portion of said artery located generally in a plane extending perpendicular to said artery, both said radiation source and detection means have axes and both of said axes are directed substantially towards the same point on the inter-wall of the artery in each of said locations, said source and said detection means also being located on the opposite side of said artery from said point at an angle relative to said artery such that radiation from said source means will be reflected back to said detection means in each of said locations, said radiation source means is separate from said radiation detection means, the axis of said source means and the axis of said detection means are located at substantially the same angle relative to a plane extending perpendicular to said artery in each of said locations, said angle is an angle from about 14.3° to 14.5°, and said radiation source means is capable of emitting a series of ultrasonic bursts of radiation and said radiation detection means is capable of providing a signal varying in amplitude according to the ultrasonic signal from each of said bursts received back by it.

16. An apparatus as claimed in claim 15 including:

grounding means for grounding the limbs of said body remote from the limb of the body on which said part of said body is located through capacitor means.

17. A process for use in making measurements on a living body having an arteriovascular circulatory system which comprises:

immobilizing part of the body in which an artery extends substantially linearly and adjacent to and substantialy parallel with the skin, locating both a radiation source and detection means adjacent to a specific location along the length of said artery which has been established as normally being capable of reflecting at least some incident radiation in an amount having physiological significance by moving said source and detection means relative to said immobilized part of said body in a coordinate system using said immobilized part of the body as a reference, said radiation source and detection means being located in a position such that radiation from said source means will be modified as a result of contact with the body in reaching said detection means, operating said radiation source and detection means so that radiation emitted by said source means is modified in reaching said detection means and is used to produce a signal at said detection means which is indicative of at least one physiological function.

18. A process as claimed in claim 17 wherein:

said part is on a limb of said body, and including grounding the other limbs of said body through capacitor means while operating said radiation source and detection means.

19. A process as claimed in claims 17 or 18 wherein:

said part of said body is immobilized by encasing said part of said body in a gauntlet like sleeve adapted to fit closely around said part of said body without interfering with the pulse of said part of said body.

20. A process as claimed in claim 17 wherein:

said radiation source and said radiation detection means are separate means, said radiation source and said detection means have axes and are located so that said axes are directed substantially toward the same point on the interior wall of said artery on the side of said artery remote from said source and detection means when said source and said detection means are operated.

21. A process as claimed in claim 20 wherein:

the axes of said source means and said detection means are located at substantially the same angle relative to a plane extending transverse to said artery at said point, said angle is an angle of from about 14° to about 14.8°.

22. A process as claimed in claim 21 wherein:

said angle is an angle of from about 14.3° to about 14.5°.

23. A process as claimed in claim 17 wherein:

said part of said body is immobilized by encasing said part of said body in a gauntlet like sleeve adapted to fit closely around said part of said body without interfereing with the pulse of said part of said body, said radiation source and said radiation detection means are separate means, said radiation source and said detection means have axes and are located so that said axes are directed substantially toward the same point on the interior wall of said artery on the side of said artery remote from said source and detection means when said source and said detection means are operated, the axes of said source means and said detection means are located at substantially the same angle relative to a plane extending transverse to said artery at said point, said angle is an angle of from about 14.3° to about 14.5°, the radiation given off by said source means and detected by said detection means is infrared radiation.

24. A process as claimed in claim 17 wherein:

said part of said body is immobilized by encasing said part of said body in a gauntlet like sleeve adapted to fit closely around said part of said body without interfering with the pulse of said part of said body, said radiation source and said radiation detection means are separate means, said radiation source and said detection means have axes and are located so that said axes are directed substantially toward the same point on the interior wall of said artery on the side of said artery remote from said source and detection means when said source and said detection means are operated, the axes of said source means and said detection means are located at substantiallay the same angle relative to a plane extending transverse to said artery at said point, said angle is an angle of from about 14.3° to about 14.5°, the radiation given off by said source means and detected by said detection means is continuous ultrasonic radiation.

25. A process as claimed in claim 17 wherein:

said part of said body is immobilized by encasing said part of said body in a gauntlet like sleeve adapted to fit closely around said part of said body without interfering with the pulse of said part of said body, said radiation source and said radiation detection means are separate means, said radiation source and said detection means have axes and are located so that said axes are directed substantially toward the same point on the interior wall of said artery on the side of said artery remote from said source and detection means when said source and said detection means are operated, the axes of said source means and said detection means are located at substantially the same angle relative to a plane extending transverse to said artery at said point, said angle is an angle of from about 14.3° to about 14.5°, the radiation given off by said source means and detected by said detection means is a series of bursts of ultrasonic radiation.

* * * * *

UNITED STATES PATENT AND TRADEMARK OFFICE
CERTIFICATE OF CORRECTION

PATENT NO. : 4,442,844
DATED : APRIL 17, 1984
INVENTOR(S) : JOSEPH H. NAVACH

It is certified that error appears in the above-identified patent and that said Letters Patent is hereby corrected as shown below:

Column 6, line 33, change "sub-frame 34" to read --sub-frame 32--;

Column 6, line 66, change the word "meters" to read --motors--;

Column 8, line 24, change "detector 90" to read --detector 94--;

Column 8, line 56, change the word "desirably" to read --desirable--;

Column 9, line 57, change the word "effect" to read --affect--;

Column 12, lines 60 and 63, change the word "package 96" to read --package 106;

Column 14, line 49, change the word "wil" to read --will--.

Column 15, line 30, delete the second occurence of the word "said".

UNITED STATES PATENT AND TRADEMARK OFFICE
CERTIFICATE OF CORRECTION

PATENT NO. : 4,442,844  
DATED : April 17, 1984  
INVENTOR(S) : Joseph H. Navach Page 2 of 2

Figure 4:
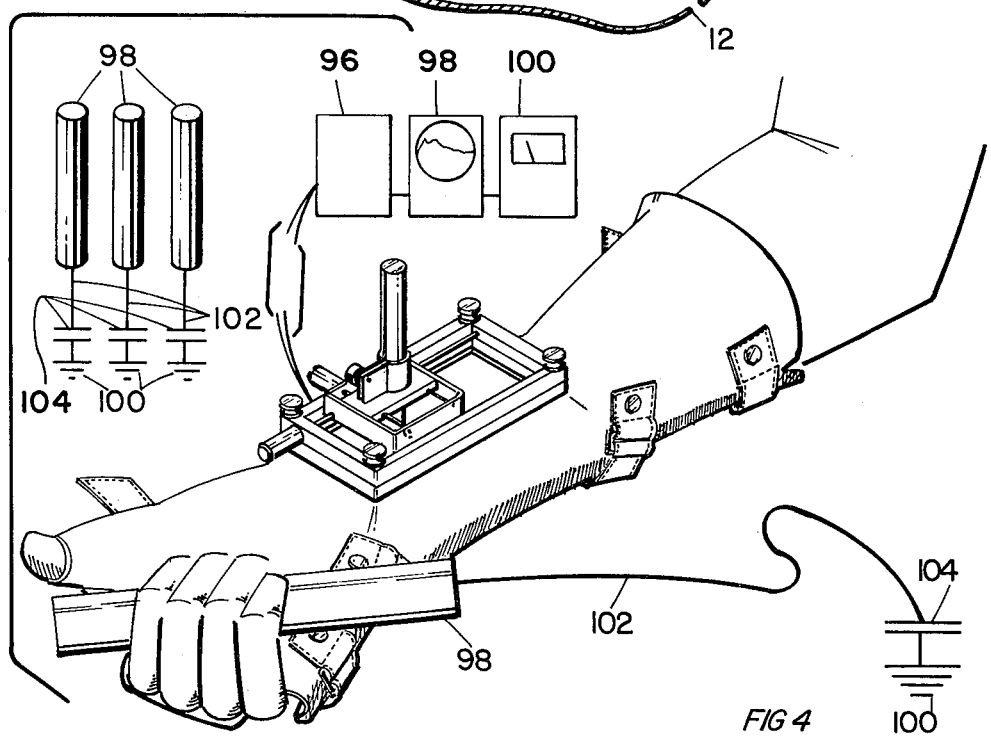
FIG. 4 is a diagrammatic view showing the apparatus illustrated in FIG. 1 in use on the human body and showing the "grounding" of this body during use of the apparatus.

It is certified that error appears in the above-identified patent and that said Letters Patent is hereby corrected as shown below:

Change the numbers "96, 98 and 100" on the three boxes at the top center portion of Fig. 4 to --106, 108 and 110-- as indicated by the following print of these boxes:

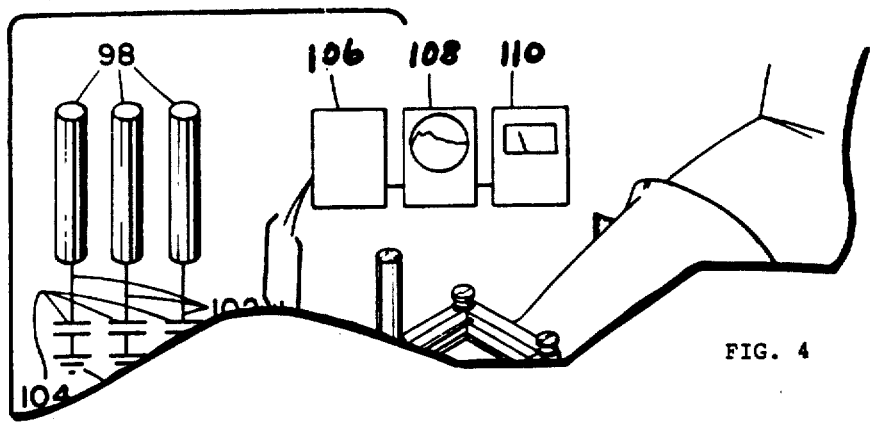

FIG. 4

Signed and Sealed this

Eleventh Day of September 1984

[SEAL]

Attest:

GERALD J. MOSSINGHOFF

Attesting Officer

Commissioner of Patents and Trademarks